US00PP09908P

United States Patent [19]

Zaiger et al.

[11] Patent Number: Plant 9,908

[45] Date of Patent: Jun. 3, 1997

[54] NECTARINE TREE "ARCTIC JAY"

[76] Inventors: Chris F. Zaiger, 929 Grimes Ave.; Gary N. Zaiger, 1907 Elm Ave.; Leith M. Gardner, 1207 Grimes Ave.; Grant G. Zaiger, 4005 California Ave., all of Modesto, Calif. 95358

[21] Appl. No.: 615,521

[22] Filed: Mar. 11, 1996

[51] Int. Cl.[6] ..... A01H 5/00

[52] U.S. Cl. ..... Plt./40.1

[58] Field of Search ..... Plt./40.1

*Primary Examiner*—James R. Feyrer

[57] ABSTRACT

A new and distinct variety of nectarine Prunus persica tree; its novelty consists of the following unique combination of outstanding features that are desirable in a new variety:

1. Fruit with excellent flavor and eating quality.
2. Fruit with a high degree of attractive red skin color.
3. The ability of the fruit to stay firm on the tree 8 to 10 days after maturity (shipping ripe).
4. Fruit with firm white flesh with good handling and shipping quality.
5. Heavy and regular production of fruit.
6. Vigorous, upright growth of the tree.

1 Drawing Sheet

ORIGIN OF THE VARIETY

The present new variety of nectarine tree was originated by us in our experimental orchard located near Modesto, Calif., as a first generation seedling from a cross between two selected seedlings with field identification numbers 38EB371 and 23K46. The maternal parent, field identification number 38EB371, originated from a cross of two selected seedlings. One originating from a nectarine of unknown parentage crossed with Redwing Peach (U.S. Plant Pat. No. 621), the other from an open pollinated O'Henry Peach (U.S. Plant Pat. No. 2,964) seedling. The paternal parent, field identification number 23K46, also originated from a cross of two selected seedlings, one originating from Golden Supreme Peach (non-patented) crossed with May Grand Nectarine (U.S. Plant Pat. No. 2,794), the other originated from a nectarine of unknown parentage crossed with Autumn Grand Nectarine (U.S. Plant Pat. No. 2,894). We grew and maintained a large group of these first generation seedlings under close and careful observation, during which time the present variety exhibited the distinctive and desirable characteristics described above and was selected for asexual reproduction and commercialization.

ASEXUAL REPRODUCTION OF THE VARIETY

The present new nectarine variety was asexually propagated by budding, as performed by us in our experimental orchard located near Modesto, Calif., and shows that all characteristics of the tree and its fruit are established and transmitted through succeeding propagations and come true to the original tree in all respects.

SUMMARY OF THE VARIETY

The herein described new variety of nectarine tree is of large size, vigorous, upright growth and a regular and productive bearer of large, white flesh, freestone fruit with excellent flavor and eating quality. The fruit is further characterized by being relatively uniform in ripening, holding firm on the tree 8 to 10 days after maturity (shipping ripe); having a high degree of attractive red skin color; and having firm white flesh with good handling and storage quality. In comparison to the Arctic Rose Nectarine (U.S. Plant Pat. No. 7,889), the new variety has greater production of larger size fruit, with a higher degree of attractive red skin color, and is approximately 8 days later in maturity.

DESCRIPTION OF THE PHOTOGRAPH

The accompanying color photograph shows a reproduction of typical specimens of the foliage and fruit of the present new nectarine variety. The illustration is of the upper and lower surface of the leaves, the exterior and sectional view of a fruit divided in the suture plane to reveal flesh coloration, pit cavity and a stone remaining in place. The photograph was taken shortly after being picked (firm ripe) and the colors are as nearly true as is reasonably possible in a color representation of this type.

DESCRIPTION OF THE VARIETY

The following is a detailed, botanical description of the new and distinct variety of nectarine tree, its flowers, foliage and fruit as based on observations of specimens grown near Modesto, Calif., with color terminology (except those in common terms) referenced to Reinhold Color Atlas by A. Kornerup and J. H. Wanscher.

Tree:
- *Size.*—Large.
- *Vigor.*—Vigorous.
- *Form.*—Upright.
- *Density.*—Medium dense.
- *Productivity.*—Productive.
- *Bearing.*—Regular.

Trunk:
- *Size.*—Medium.
- *Texture.*—Medium shaggy.
- *Color.*—Brown to soot brown (5-E-5) to (5-F-6).

Branches:
- *Size.*—Medium.
- *Texture.*—Smoth to medium rough.
- *Lenticels.*—Numerous. Large size.
- *Color.*—Light brown to brown, varies with age of growth (5-D-5) to (5-D-7).

Leaves:
- *Size.*—Large. Average length — 6¼". Average width — 1⅝".
- *Form.*—Lanceolate, pointed.
- *Texture.*—Smooth.
- *Margin.*—Crenate.
- *Petiole.*—Medium length. Medium thickness.

*Glands.*—Number varies from 1 to 5. Average number 3. Reniform. Located on upper portion of petiole and lower portion of leaf blade.

*Color.*—Upper surface — green to dark green (28-F-7) to (28-F-8). Lower surface — light green to dull green (28-E-6) to. (28-E-7).

Flower buds:

*Size.*—Medium to large.

*Length.*—Medium.

*Form.*—Plump.

Flowers:

*Size.*—Large, showy.

*Blooming period.*—Date of first bloom: Mar. 4, 1994. Date of last bloom: Mar. 9, 1994. Varies slightly with climatic conditions.

*Pollen.*—Present, self-fertile.

*Color.*—Pink.

Fruit:

*Maturity when described.*—Firm ripe.

*Date of first picking.*—Jul. 7, 1994.

*Date of last picking.*—Jul. 13, 1994. Maturity varies slightly with climatic conditions.

*Size.*—Large. Average diameter axially — 3⅛". Average transversely in suture plane — 3".

*Form.*—Nearly globose, slightly flattened at stem end.

*Suture.*—Shallow, extends from base to apex.

*Ventral surface.*—Nearly round, varies from round to slightly lipped.

*Base.*—Retuse.

*Cavity.*—Round to slightly elongated in suture plane. Average depth — ½". Average breadth — ⅞".

*Apex.*—Usually slight pistil point, varies from slight pistil point to rounded.

Flesh:

*Ripens.*—Evenly.

*Texture.*—Firm.

*Fibers.*—Few, small, tender.

*Juice.*—Moderate.

*Flavor.*—Excellent, mild, sweet, sub-acid.

*Eating quality.*—Excellent.

*Aroma.*—Moderate.

*Amygdalin.*—Undetected.

*Color.*—White to milk white (1-A-1) to (1-A-2). Pit cavity, light red to red (10-A-6) to (10-A-7). Slight bleeding of red into flesh around pit cavity, heavier toward apex.

Skin:

*Thickness.*—Medium.

*Texture.*—Medium, tenacious to flesh.

*Tendency to crack.*—None.

*Down.*—Wanting.

*color.*—White to yellowish white ground color (4-A-1) to (4-A-3). Overspread with red to bronze red (10-C-8) to (10-D-7).

Stone:

*Type.*—Freestone.

*Size.*—Large. Average length — 1½". Average width — 1⅛". Average thickness — ⅝".

*Form.*—Obovoid.

*Base.*—Usually straight, varies from straight to rounded.

*Apex.*—Cuspidate.

*Sides.*—Equal to unequal.

*Surface.*—Furrowed toward apex. Long, deep furrow on each side of suture plane. Pitted throughout, pits vary from round to elongated.

*Ridges.*—Rounded.

*Tendency to split.*—Very slight.

*Color.*—Brownish red to reddish brown (8-D-6) to (9-C-6).

Use: Dessert.

*Market.*—Local and long distance.

Keeping quality: Good.

Shipping quality: Good.

The present new and distinct variety of nectarine tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of nectarine tree, substantially as illustrated and described, characterized by its large size, vigorous, upright growth and being a productive and regular bearer of large, firm, white flesh, freestone fruit with excellent flavor and eating quality; the fruit is further characterized by having good handling and shipping quality, having an attractive red skin color and, in comparison to Arctic Rose Nectarine (U.S. Plant Pat. No. 7,889), the new variety has greater production of larger size fruit, a higher degree of attractive red skin color and is approximately 8 days later in maturity.

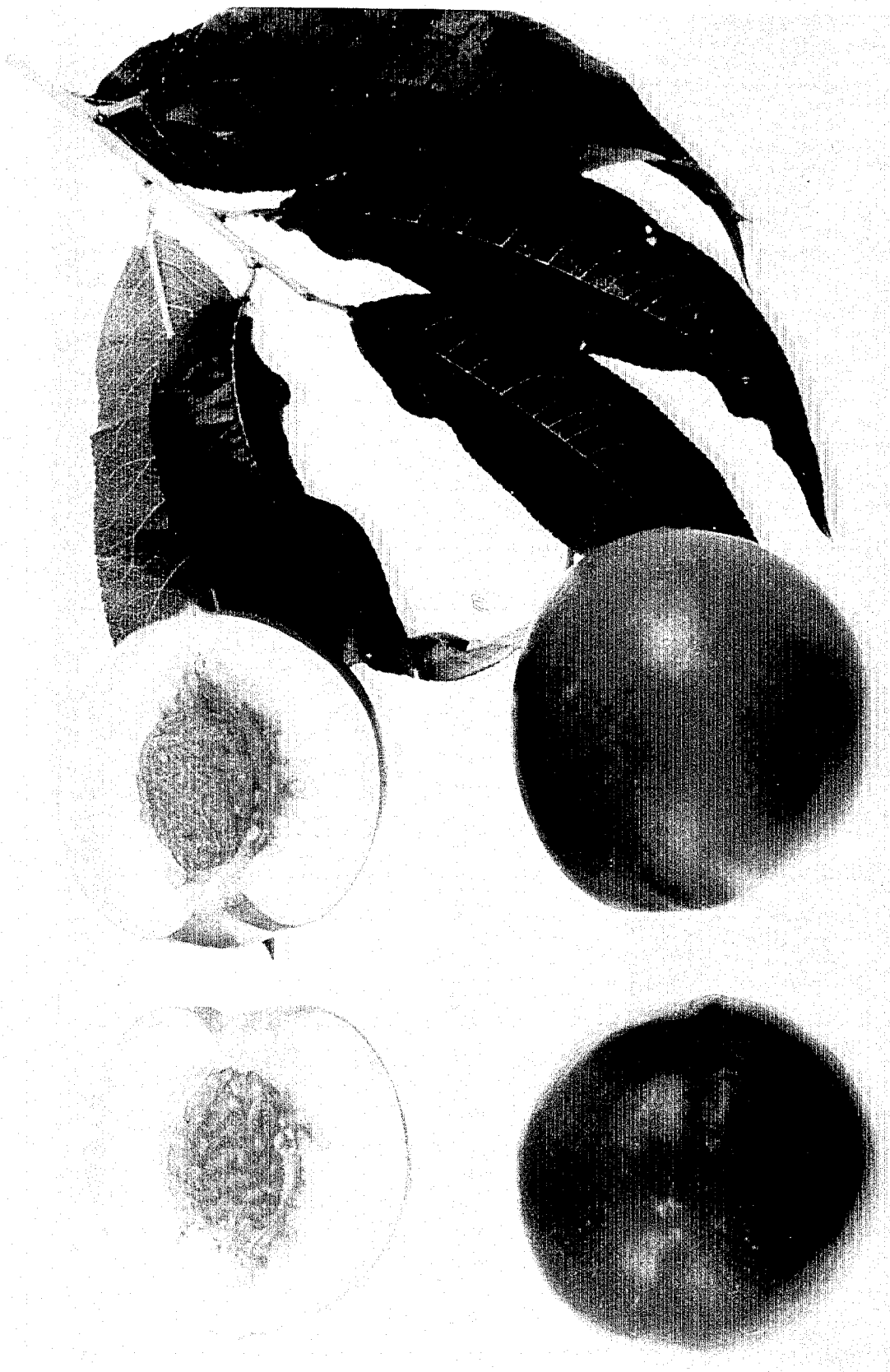

* * * * *